United States Patent [19]

Brull

[11] Patent Number: 4,590,804
[45] Date of Patent: May 27, 1986

[54] DEVICE FOR MONITORING FATIGUE LIFE

[75] Inventor: Maurice A. Brull, Herzliya Pituach, Israel

[73] Assignee: Tensiodyne Scientific Corporation, Philadelphia, Pa.

[21] Appl. No.: 573,081

[22] Filed: Jan. 23, 1984

[51] Int. Cl.[4] ............................................. G01N 19/08
[52] U.S. Cl. ...................................... 73/762; 73/786; 73/787; 73/799
[58] Field of Search ................. 73/762, 786, 787, 799, 73/802

[56] References Cited

U.S. PATENT DOCUMENTS

| | | | |
|---|---|---|---|
| 2,294,897 | 9/1942 | Ellis | 73/762 |
| 2,920,480 | 1/1960 | Haas | 73/787 |
| 2,986,926 | 6/1961 | Freemon | 73/799 |
| 2,986,928 | 6/1961 | White | 73/794 |
| 3,034,340 | 5/1962 | Jankowsky et al. | 73/799 |
| 3,136,154 | 6/1964 | Christensen | 73/802 |
| 3,482,437 | 12/1969 | Martens . | |
| 3,572,091 | 3/1971 | McFarland . | |
| 3,774,443 | 11/1973 | Green et al. | 73/799 |
| 3,786,679 | 1/1974 | Crites | 73/787 |
| 3,803,485 | 4/1974 | Crites et al. | 73/762 |
| 3,918,299 | 11/1975 | Donnadieu | 73/799 |
| 3,979,949 | 9/1976 | Smith | 73/762 |
| 4,107,980 | 8/1978 | Crane et al. | 73/762 |
| 4,164,874 | 8/1979 | Cassatt et al. | 73/799 |
| 4,255,974 | 3/1981 | Dufrane et al. | 73/799 |
| 4,322,981 | 4/1982 | Radwill | 73/799 |
| 4,343,424 | 8/1982 | Montemarano et al. | 73/799 |

Primary Examiner—Anthony V. Ciarlante
Attorney, Agent, or Firm—Panitch Schwarze Jacobs & Nadel

[57] ABSTRACT

A device for monitoring the fatigue life of a structural member is comprised of at least one and preferably a plurality of substantially flat, elongated coupons which are fabricated of the same material as that of the member being monitored. The coupons are secured in parallel to the member so that they all experience the same strain history as the member. Each of the coupons includes a different stress concentrating notch pattern so that the application of the same strain to all of the coupons results in the development of different stress concentrations within the coupons. The development of different stress concentrations within the coupons causes each coupon to have a different fatigue life, the fatigue life of each coupon being a predetermined percentage of the fatigue life of the structural member being monitored.

17 Claims, 3 Drawing Figures

DEVICE FOR MONITORING FATIGUE LIFE

BACKGROUND OF THE INVENTION

The present invention relates to fatigue monitoring and, more particularly, to a device for providing an indication of the progression of fatigue damage within a structure and a method for making such a device.

Potential structural failure due to fatigue constitutes one of the most troublesome areas of structural engineering primarily because fatigue failure occurs suddenly, usually in critical areas of a structure. Although many aspects of fatigue are still unknown, it is generally understood that the fatigue process starts with the microscopic imperfections or defects which are present in all materials. Under certain circumstances, the microscopic imperfections rapidly grow and coalesce to form a macroscopic defect in the form of a crack. The growth and propagation of macroscopic cracks is the immediate cause of a fatigue failure. However, the appearance of such macroscopic cracks occurs relatively late in the fatigue process and, therefore, cannot be used as an acceptable warning device of impending fatigue failure.

The primary factor which causes the inherent microscopic material defects to grow and coalesce is the presence of an intense stress or strain field (hereinafter collectively referred to as a "stress field"). Such intense stress fields or stress concentrations generally occur in the vicinity of sudden discontinuities or "stress raisers" such as holes, notches or other similar geometric discontinuities within a structural configuration. Thus, fatigue failure generally originates at or near such stress raisers and is believed to begin whenever a certain critical stress or critical strain is exceeded. Fatigue is therefore a primary design consideration in many applications which involve repeated and often varying loadings such as aircraft, machine elements, pressure vessels, bridges, etc.

In the past, structural designers have attempted to circumvent the problem of fatigue failure by designing structures in a manner which maintains the stresses present in the critical areas of a structure at a level well below the known endurance limits of the material employed. Hence, minimum radius holes, fillets etc. are introduced into structural designs and only "mild" stress raisers are employed in the structure in order to provide relatively smooth structures and to thereby decrease the likelihood of fatigue failure. While this type of design approach results in structures which are generally safe and relatively free of fatigue failure, it also results in unacceptable penalties in structural efficiency which, in turn, result in excessive structural costs.

When designing a structure to compensate for fatigue and in trying to assess the potential fatigue life of the structure, a designer generally relies on a combination of experimental data and previously developed empirical design rules. Experimental fatigue data have been accumulated on most structural materials in the form of S-n curves which provide an indication of the number of loading cycles which will induce fatigue failure as a function of the stress level applied to the material. The experimental data, however, exhibit a significant amount of scatter and are only strictly applicable to structures where the cyclic stress applied to the structure is of a constant amplitude. Most actual structures which are subjected to repeated loadings generally experience varying levels of stress for different numbers of cycles. Thus, the fatigue life of a particular structure greatly depends upon its specific individual stress history.

In applying the experimental S-n curve data to actual loading situations, empirical rules and procedures have been suggested. These empirical rules, referred to as cumulative damage rules, (the most common of which is Minor's Rule), have also been found to be inadequate. Even in the simplest case of two different stress levels applied to a structure, it has been demonstrated experimentally that structural fatigue life is dependent on the order of application of the stress levels. None of the known cumulative damage rules take into account the potential differences in the order of application to the structure of differing stress levels. Moreover, cumulative fatigue damage cannot be determined by non-destructive testing so that, short of conducting a detailed microscopic examination of the structure of the material, there is no known way to accurately determine the cumulative damage of a structural member at a given time.

In summary, in addition to being inefficient, the practice of designing structures to take into account fatigue is highly speculative since the actual loading history of the structure is not known and cannot be accurately predicted. Therefore, there is a need for a device which would monitor fatigue damage and provide a reliable estimate of the remaining fatigue life of a particular structure in order to provide a warning of impending fatigue failure in sufficient time to permit measures to be taken, such as the repair or replacement of such structures, to minimize the possibility of catastrophic consequences.

The present invention comprises a relatively simple fatigue monitoring device which can provide a repeatable, reliable estimate of the remaining fatigue life for any desired structural member. The device is attached to the structural member whose fatigue life is to be monitored so that the device is subjected to the exact same strain history and environment experienced by the actual structural member. The device is small and inexpensive to manufacture and can be specifically tailored to particular structural applications and structural materials as required.

SUMMARY OF THE INVENTION

Briefly stated, the present invention is a device for monitoring the fatigue life of a member. This device is comprised of at least one and preferable a plurality of substantially flat, elongated coupons fabricated of the same material as the member being monitored, the coupons being mounted in parallel on the member so that all of the coupons experience the same strain history as the member being monitored. Each of the coupons includes a special notch pattern comprised of at least one pair of notches designed to produce a local stress concentration. One notch of each of the notch pairs is disposed on each of the longitudinal sides of the coupon, the notches of the notch pair being substantially geometrically the same. Their axis must be oriented along a suitably chosen direction. The notch pattern of each of the coupons produces a stress field which varies in intensity from relatively mild to very severe. The severity of the local stress field is controlled by the geometry of the notch pattern. Smooth geometries produce mild stress concentration, while sharp geometric discontinuities produce severe stresses. In this manner, the application of the same strain history to all of the coupons results in the development of different stress concentrations in the region of the notch tips of each coupon, so that each coupon has a different fatigue life. The fatigue life of each coupon is a percentage of the fatigue life of the member being monitored. The present invention also comprises a method for making the previously described device.

BRIEF DESCRIPTION OF THE DRAWING

The foregoing summary, as well as the following detailed description will be better understood when read in conjunction with the appended drawing. For the purpose of illustrating the invention, there is shown in the drawing an embodiment which is presently preferred, it being understood, however, that this invention is not limited to the precise arrangement shown. In the drawing.

DESCRIPTION OF A PREFERRED EMBODIMENT

Figure 1:
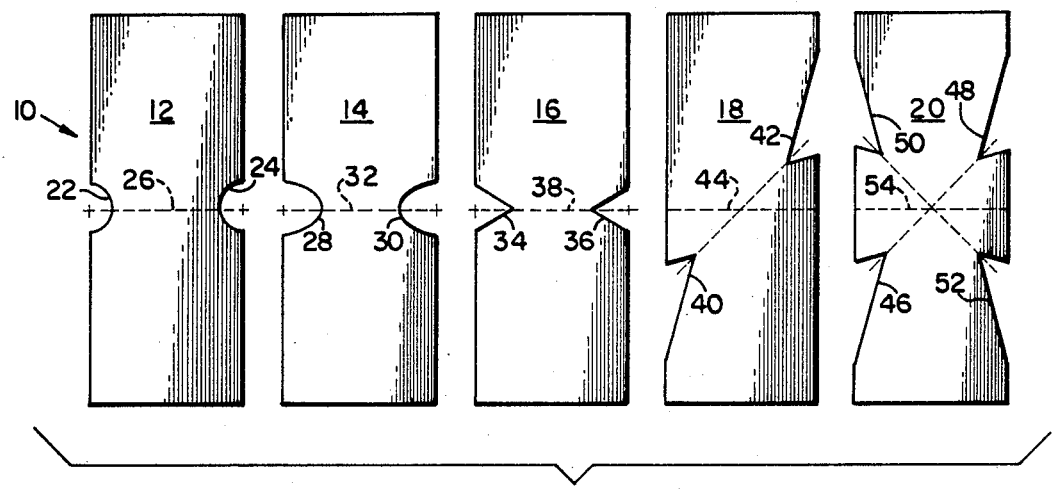
FIG. 1 is a plan view of five generally parallel coupons which comprise a preferred embodiment of a fatigue monitoring device in accordance with the present invention.

Referring to FIG. 1, there is shown a device 10 for monitoring the fatigue life of a structural member (not shown). The fatigue monitoring device 10 is comprised of a plurality of individual coupons 12, 14, 16, 18 and 20, five such coupons being presently preferred. The coupons 12, 14, 16, 18 and 20 are substantially flat (preferably about 0.5 mm in thickness) and are generally rectangular in shape with a longitudinal length of about 25 mm and a lateral width of about 6.5 mm. While the preceding dimensions for the coupons are presently preferred, it should be understood that the length, width and thickness of the coupons many vary for a particular application, the present invention not being limited to coupons of any particular dimensions.

The coupons 12, 14, 16, 18 and 20 are preferably fabricated of the same material as the structural member (not shown) which is being monitored. In the presently preferred embodiment, the structural member being monitored (not shown) is comprised of a high strength aluminum alloy known as 7075-T6 aluminum which is used extensively in the construction of aircraft and other structures which require high strength and light weight. The use of 7075-T6 aluminum in connection with the presently preferred embodiment is only for purposes of illustrating the principles of the present invention it being clearly understood that the coupons may be fabricated of any other material, such as other metals, plastic etc., preferably the same material as that employed in the particular structural member to be monitored.

The coupons 12, 14, 16, 18 and 20 are combined into a single gauge which is located in such a manner as to experience the same actual strain history and environment as is experienced by the structural member (not shown) which is being monitored. Generally, this means that the coupons are mounted on or secured directly to the structural element being monitored and remain with the structural element throughout its service life (not shown). The coupons may be secured to the member by pins or any other suitable type of bond such as an adhesive bond or spot weld. In order to assure that each of the coupons experiences the same strain history, the coupons should be mounted or attached to each other in parallel and secured to the member being monitored. The device need not be mounted at the critical section of the structural element being monitored but should be mounted in such a manner as to experience the same strain history and environment as the member. Preferably, the coupon axes are oriented in the direction of the maximum principal tensile strain which is expected to be experienced by the member being monitored. By locating the coupons as described, the previously described difficulties involved in determining the cumulative damage of the structural member being monitored are avoided.

The basic premise of the invention is to insure that, since the basic principles of fatigue are not clearly understood in sufficient detail to accurately determine cumulative damage and to predict remaining fatigue life, fatigue should be monitored in such a manner that the monitoring device 10 has the same characteristics as the member being monitored and experiences the same strain history and environment. However, accelerated fatigue damage is produced within the device 10 by introducing into each coupon 12, 14, 16, 18 and 20 a predetermined stress raiser or stress concentrating notch pattern which produces an intense stress concentration or stress intensity field within the coupon. The introduction of such a stress raiser insures that each of the coupons has a shorter fatigue life than the structural member being monitored, assuming that the coupons and the member are subjected to the same strain history. By varying the severity of the stress raisers (i.e. varying the notch pattern) within the individual coupons, each coupon can be specifically tailored to experience fatigue failure at a fairly accurate and repeatable portion or percentage of the expected life of the structural member being monitored. Thus, the failure of each coupon provides a generally reliable indication of the expiration of a portion of the fatigue life of the structural member being monitored.

The fatigue failure of the individual coupons can be detected in any suitable manner, for example, by visual inspection or by the use of a remote means, to provide an indication of the portion or percentage of the fatigue life of the structural member being monitored which has expired and to thereby indicate the expected remaining fatigue life of the structural member or to give warning of impending fatigue failure. If the severity of the stress raisers introduced into the coupons is varied over a suitable range extending from slightly more severe than the stress raisers present in the member being monitored and increasing in severity in steps, the fatigue life of the member can be monitored relatively accurately. As will hereinafter become apparent, the severity of the stress raisers is controlled primarily by the geometry of the notches within the coupons. As will also hereinafter become apparent the geometry of the stress raisers varies depending upon the particular material of the structural member being monitored and may be predetermined in accordance with the principles of this invention as hereinafter set forth in detail.

The coupons 12, 14, 16, 18 and 20 of the present embodiment are arranged in order with the severity of the notch pattern increasing from left to right (i.e. the severity of the notch pattern in coupon 14 is greater than that of coupon 12 etc.). Thus, the coupons 12, 14, 16, 18 and 20 of the present embodiment are expected to reach their respective fatigue failure points in the reverse order (i.e. coupon 20 will fail first etc.). The severity of the notch pattern ranges from relatively mild, having no significant geometric discontinuities as shown in the smooth, semicircular notches 22 of coupon 12, to relatively severe, having a plurality of sharp geometric discontinuities as indicated by the multiple V-shaped notches of coupon 20.

The primary reason for the variations in the notch pattern is the significant difference in physical behavior and mathematical description of the stresses which are experienced by the coupon in the vicinity of the notches. In the case of a coupon 12 having mild notches, the area near the notch tips experience a local increase in stress varying from the undisturbed stress to a maximum occurring at the edge of the notch. This maximum value can be expressed by the equation:

$$\sigma_y = c\sigma$$

where:
$\sigma_y$ is the stress present at the notch tip which is the maximum stress in the coupons;
$\sigma$ is the uniform tension applied upon the ends of the coupon; and
C is a stress concentration factor.

The variation of the stress from its maximum value to the undisturbed value $\sigma$ is a function which depends on the exact notch geometry. For semi-circular or semi-elliptical notches that function is a polynomial.

In contrast to the coupon 12 having a mild notch pattern, the stresses introduced into a coupon 20 having a severe notch pattern consisting of sharp discontinuities in the boundaries is given by an equation of this type:

$$\sigma_n = K/X^n$$

where:
$\sigma_n$ is the stress along the line between the notches;
X is a coordinate with origin at the notch tip and directed along the line between notch tips;
K is a stress intensity factor; and
n denotes the rate at which the stresses increase near the notch tip (this is often called the order of the stress singularity).

As is apparent from the foregoing equation, in a coupon having a severe notch pattern, the stress tends to become infinite at the notch tip and would do so if there were no limit to the strength of the material. In reality this stress is limited by the material causing either the notch to propagate as a crack or the creation of a plastic zone in which fatigue damage accumulates rapidly.

It has been found experimentally that the features of the stress near between the notches are controlled by either the stress concentration factor (for mild notches) or the stress intensity factor (for severe notches) and by the rate at which the stresses decay back to their average (undisturbed) value as the distance from the notches is increased. These two factors control the rate at which damage accumulates in a coupon near a notch and, therefore, the time required to produce a macro crack and a subsequent fatigue failure within the coupon. Thus, given that a certain critical stress is required to cause a microscopic defect within the coupon to grow, the stress intensity or stress concentration factor governs the overall magnitude of the stress field created while the rate of decay of the stresses determines how close to the notch a defect must be in order to cause the defect to grow. Assuming that the microscopic defects are distributed in a statistically homogeneous fashion throughout the coupon material, the combination of the two factors can be viewed as a measure of the probability that fatigue damage will occur within the coupon in the area between the notches. The desired result is to obtain a sequence of practical notch patterns within the coupons which provide control of these critical factors to insure that the fatigue lives of the coupons are all different but all significantly shorter than the fatigue life of the structural member being monitored.

It has been found that certain geometric features of the notches can be changed to vary the severity of the notch pattern. For example, it has been found that if the notches are aligned with each other at a zero degree orientation angle $\theta$ as shown in coupon 16 the critical parameters are relatively insensitive to changes in the wedge angle $\alpha$ of the notches. On the other hand, if the notches are positioned to be aligned at an orientation angle of 45 degrees from the perpendicular as shown on coupon 18, the loading between the notches is in shear rather than in tension and the rate of decay of the stresses is strongly affected by the wedge angle of the two notches. Thus, the two controlling parameters with respect to the variations in the notch pattern are the notch or wedge angle $\alpha$ and the orientation of the notches or orientation angle $\theta$. By using a series of notches with differing wedge angles and orientation angles, the fatigue life of the individual coupons can be varied and controlled to provide coupons with fatigue lives which are different predetermined percentages of the fatigue life of the structural member being monitored.

Viewing FIG. 1 it can be seen that the coupons 12, 14, 16, 18 and 20 each have a different notch pattern. Coupon 12 has the mildest notch pattern which comprises a single pair of notches 22 and 24 which are each substantially semicircular in shape and of the same size so that the notches 22 and 24 are substantially geometrically the same. In addition, the notches 22 and 24 are substantially aligned with each other along a single laterally extending axis 26 to provide a zero degree orientation angle. One of the notches is disposed on each of the longitudinal sides of the coupon 12 as shown. As previously discussed, semicircular notches 22 and 24 or this type are considered to be mild stress raisers in that they are relatively smooth and contain no sharp geometric discontinuities. Thus, in accordance with the foregoing discussion, coupon 12 can be expected to have a fatigue life representative of a structural element with a mild stress raiser and this life will be longer than the fatigue life of any of the other coupons which will hereinafter be described.

Coupon 14 similarly includes a relatively mild notch pattern comprised of single pair of notches 28 and 30, one of which is disposed on each of the longitudinal sides of the coupon 14. Again, the notches 28 and 30 are directly aligned along a single lateral axis 32 to provide a zero degree orientation angle. However, unlike the semicircular notches 22 and 24 of coupon 12, the two notches of coupon 14 are each substantially semi-elliptically shaped both being of the same approximate size. While still considered to be a mild stress raiser, the semi-elliptically shaped notches 28 and 30 have a higher stress calculation factor than the smooth semicircular shaped notches 22 and 24 of coupon 12. Therefore, when subjected to the same stress history, coupon 14 can be expected to have a shorter fatigue life than that of coupon 12. Of course, the fatigue life of coupon 14 also constitutes an approximate predetermined percentage of the fatigue life of the structural member being monitored.

Coupon 16 also includes a notch pattern comprised of a single pair of notches 34 and 36 disposed on each of the longitudinal sides of the coupon. As with the notches of coupons 12 and 14, the notches 34 and 36 are generally aligned along a single axis 38 (zero degree orientation angle) which is perpendicular to the longitudinal coupon sides as shown. However, unlike the notches of coupons 12 and 14, notches 34 and 36 are wedge or V-shaped to provide a relatively sharp geometric discontinuity. In the present embodiment the wedge angle $\alpha$ of notches 34 and 36 is 60 degrees, it being understood that the present invention is not limited to notches having a particular wedge angle. The stress field concentration between the notches 34 and 36 is greater than that of coupons 12 and 14, so coupon 16 can be expected to have a shorter fatigue life than that of either coupon 12 or 14.

Figure 2:
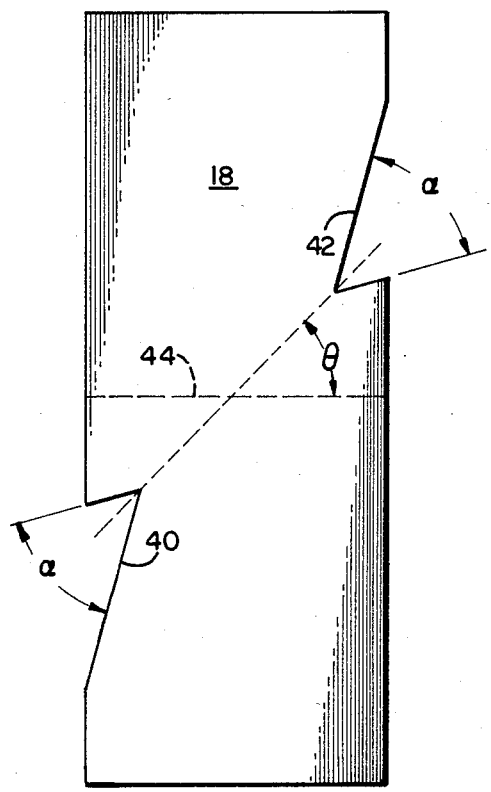
FIG. 2 is an enlarged plan view representation of one of the coupons of FIG. 1.

Coupon 18, which is shown in greater detail in FIG. 2, has a notch pattern comprised of a single pair of notches 40 and 42 each of which is generally V-shaped with a 60 degree wedge angle. Unlike the previously discussed coupons, the notches of coupon 18 are aligned with each other at approximately a 45 degree angle with respect to the lateral axis 44 extending across the coupon 18. It can be expected that coupon 18 will have a shorter fatigue life than any of the coupons 12, 14 or 16 previously described.

Coupon 20 has a notch pattern comprised of two pairs of notches 46/48 and 50/52. Each of the notches is generally V-shaped with a 60 degree wedge angle. The notches of each pair are respectively aligned at orientation angles of plus or minus 45 degrees from the lateral axis of the coupon 54. The notch pattern of coupon 20 produces the greatest stress field intensity in the area between the notch pairs and, therefore, coupon 20 can be expected to have a shorter fatigue life than any of the other coupons 12, 14, 16 or 18.

Coupons 12, 14, 16, 18 and 20 fabricated of 7075 aluminum were constructed and employed to monitor the fatigue life of a structural member which was also constructed of 7075 aluminum. The coupons 12, 14, 16, 18 and 20 were combined into a gauge and mounted on a structural member which was also constructed of 7075 aluminum. When a fatigue test of the member was conducted of the beam with the device mounted on it, failure of the various coupons occurred at the number of cycles indicated in the following table:

| Coupon # | Cycles to Coupon Fatigue Failure |
| --- | --- |
| 12 | 371,600 cycles |
| 14 | 286,700 cycles |
| 16 | 203,900 cycles |
| 18 | 174,600 cycles |
| 20 | 163,600 cycles |

Figure 3:
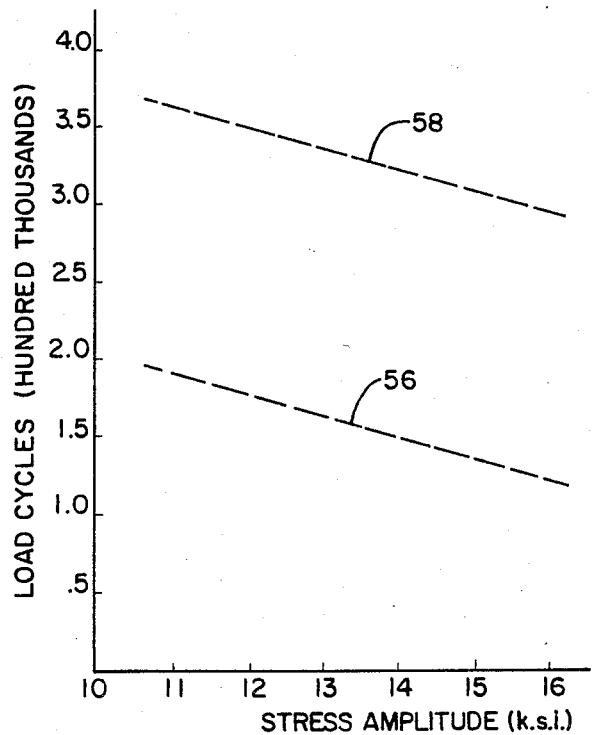
FIG. 3 is a graphic representation of a portion of a typical load cycle versus stress amplitude relationship (S-n curve) for two of the coupons of FIG. 1.

The structural member being monitored suffered fatigue failure at 486,000 cycles. Examination of the test data indicates that coupons provided fatigue damage warnings at approximately 33% (coupons 18 and 20), 60% (coupons 14 and 16) and 75% (coupon 12) of the actual fatigue life of the structural member being monitored. Additional testing verified that the results set forth above are repeatable to provide a relatively reliable indication of remaining fatigue life. A portion of a typical S-n curve for coupons 20 and 14 are shown in FIG. 3, line 56 representing the S-n curve for coupon 20 and line 58 representing the S-n curve for coupon 14. As previously discussed, S-n curves provide an indication of the number of load cycles which will induce fatigue failure as a function of the applied stress level.

Although the foregoing description of a preferred embodiment of the present invention relates to a set of coupons 12, 14, 16,18 and 20 fabricated of 7075 aluminum for the purpose of monitoring the fatigue life of a structural member of 7075 aluminum, it will be appreciated that the same concepts and techniques are applicable with respect to other materials. It will also be appreciated that the notch patterns, including the number of notch pairs, the geometry of the notches, the wedge angles $\alpha$ and the notch orientation angles $\theta$ may vary with other materials. Coupons may be produced utilizing the below described method for use in connection with other materials which are subject to fatigue failure.

In addition, although the preferred embodiment employs a set of five coupons it should be appreciated that a greater or lesser number of coupons could be utilized, depending upon the particular application. For example, in a particular situation it may be necessary to identify only the 60 percent point of the fatigue life of a particular member. In such an application only a single coupon having a notch pattern which indicates the expiration of approximately 60% of the life of the member could be employed. However, it is preferable to employ more than a single coupon in order to show progressive damage, to guard against any undetected severe defect which might be present in the structural member and generally to provide added confidence and safety.

In developing a set of coupons for monitoring the fatigue life of a member of any particular material, a thin sheet of the particular material (preferably 0.5 mm thick) is obtained and a plurality of elongated coupons approximately 25 mm by 6.5 mm are fabricated from the thin sheet of the material. Sets of five of the coupons are cut from the sheet and notches are cut into the five coupons in each set in the manner as is described above with respect to coupons 12, 14, 16, 18 and 20.

After the sets of five notched coupons have been fabricated, fatigue tests are run on each coupon within each set to produce an S-n endurance curve for each of the five different coupons to indicate the number of cycles to develop fatigue failure in the coupons as a result of the applied stress level. When the S-n curves have been produced for each coupon, they are examined to determine whether the separation between the failure of the different coupons is adequate to provide the desired separation of the early fatigue failure warnings. If the separation is satisfactory, a new set of five coupons having the same notch pattern is produced and each of the coupons are subjected to common fatigue testing under controlled strain at various strain amplitudes to again verify the order in which the coupons suffer fatigue failure. Thereafter, another set of the coupons may be fabricated and fatigue tested on a small-scale specimen of the structural member to be monitored to verify the particular portion or percentage of the fatigue life of the structural member at which each of the coupons will experience fatigue failure.

If, upon the initial testing it is found that the separation between the S-n curves of the coupons is not satisfactory and further refinements and modifications of the coupon life are desired, the notch pattern on one or more of the coupons may be changed. Depending upon whether it is desired to increase or decrease the fatigue life of a particular coupon, the wedge angle $\alpha$ could be modified or the orientation angle $\theta$ could be changed, or both. As previously indicated, smaller wedge angles represent more severe stress raisers and therefore shorter fatigue life. In addition, changes in the orientation angles $\theta$ represent different combinations of tension and shear on the line between the notch tips, resulting in varying sensitivity to the wedge angle and varying rates of decay of the stress near the notch tips. These parameters thus control the probability of growth of microdefects. Once the modifications have been made, further fatigue testing is conducted to generate new S-n curves and the remainder of the above-described process is conducted.

From the foregoing description of a preferred embodiment it can be seen that the present invention comprises a device for monitoring the fatigue life of a structural member which is subject to fatigue failure. The device contains no moving parts and is relatively simple and inexpensive to produce but yet provides a good indication of the remaining fatigue life of the structural member being monitored. The present invention also provides a method for developing a set of coupons for monitoring the fatigue life of a structural member which may be made of any type of material. It will be recognized by those skilled in the art that changes may be made to the above-described embodiment of the invention without departing from the broad inventive concepts thereof. It is understood, therefore, that this invention is not limited to the particular embodiment disclosed, but is intended to cover all modifications which are within the scope and spirit of the invention as defined by the appended claims.

I claim:

1. A device for monitoring the fatigue life of a member comprising a plurality of substantially flat, elongated coupons fabricated of the same material as the member being monitored, the coupons being secured in parallel to the member so that all of the coupons experience the same strain history as the member, each of the coupons having a stress concentrating notch pattern comprised of at least one pair of notches, one notch of the notch pair being disposed on each of the longitudinal sides of a coupon, the notches of the notch pair being substantially geometrically the same and substantially aligned with each other, the notch pattern of each of the coupons varying in intensity from mild, in which the edge surfaces of the notches are generally smooth and continuously curved, to severe, in which the edge surface of each of the notches exhibits a sudden change to form two portions which are in different planes, the two portions meeting to form a line so that the application of the same strain to all of the coupons results in the development of different stress concentrations near the notches of each coupon so that each coupon has a different fatigue life, the fatigue life of each coupon being a percentage of the fatigue life of the member being monitored.

2. The device as recited in claim 1 wherein five coupons are employed.

3. The device as recited in claim 2 wherein two of the coupons have a mild notch pattern and three of the coupons have a severe notch pattern.

4. The device as recited in claim 1 or 3 wherein one of the coupons has a notch pattern comprised of a pair of substantially semicircular-shaped notches aligned along a common lateral axis with a substantially zero degree orientation angle.

5. The device as recited in claim 1 or 3 wherein one of the coupons has a notch pattern comprised of a pair of substantially elliptically-shaped notches aligned along a common lateral axis with an orientation angle of substantially zero degrees.

6. The device as recited in claim 1 or 3 wherein one of the coupons has a notch pattern comprised of a pair of V-shaped notches aligned along a common lateral axis with a substantially zero degree orientation angle.

7. The device as recited in claim 6 wherein the wedge angle of the V-shaped notches is substantially 60 degrees.

8. The device as recited in claim 1 or 3 wherein one of the coupons has a notch pattern comprised of a pair of V-shaped notches aligned at substantially a 45 degree orientation angle with respect to the lateral axis.

9. The device as recited in claim 8 wherein the wedge angle of the notches is substantially 60 degrees.

10. The device as recited in claim 1 or 3 wherein one of the coupons has a notch pattern comprised of two pairs of V-shaped notches, one notch from each pair being disposed on each longitudinal side of the coupon, the notches of each pair being aligned with each other at substantially plus or minus 45 degree angle with respect to the lateral axis.

11. The device as recited in claim 10 wherein the wedge angle of each of the notches is substantially 60 degrees.

12. A device for monitoring the fatigue life of a member comprising a plurality of substantially flat, elongated coupons fabricated of the same material as the member being monitored, the coupons being secured to the member so that each of the coupons experiences the same strain history as the member, each of the coupons having a stress concentrating notch pattern comprised of at least one pair of notches, one notch of the notch pair being disposed on each of the longitudinal sides of each coupon, the notches of the notch pair of each coupon being substantially geometrically the same and substantially aligned with each other, so that the application of strain to the member being monitored and to the coupons results in the development of a stress concentration near the notches each coupon comprising a different geometrical pattern of notches such that each coupon experiences a different stress concentration as the member is being monitored.

13. The device as recited in claim 12 wherein a coupon notch pattern is comprised of a pair of substantially V-shaped notches.

14. The device as recited in claim 13 wherein the V-shaped notches have a wedge angle of substantially 60 degrees.

15. The device as recited in claim 14 wherein the V-shaped notches are aligned at an orientation angle of substantially zero degrees with respect to the lateral axis.

16. The device as recited in claim 14 wherein the V-shaped notches are aligned at an orientation angle of substantially 45 degrees with respect to the lateral axis.

17. The device as recited in claim 12 wherein a notch pattern comprises two pairs of V-shaped notches, one notch from each pair being disposed along each longitudinal side of the coupon, the V-shaped notches having a substantially 60 degree wedge angle, the notches of each pair being aligned with each other at a substantially plus or minus 45 degree orientation angle with respect to the lateral axis of the coupon.

* * * * *